Figure 1:
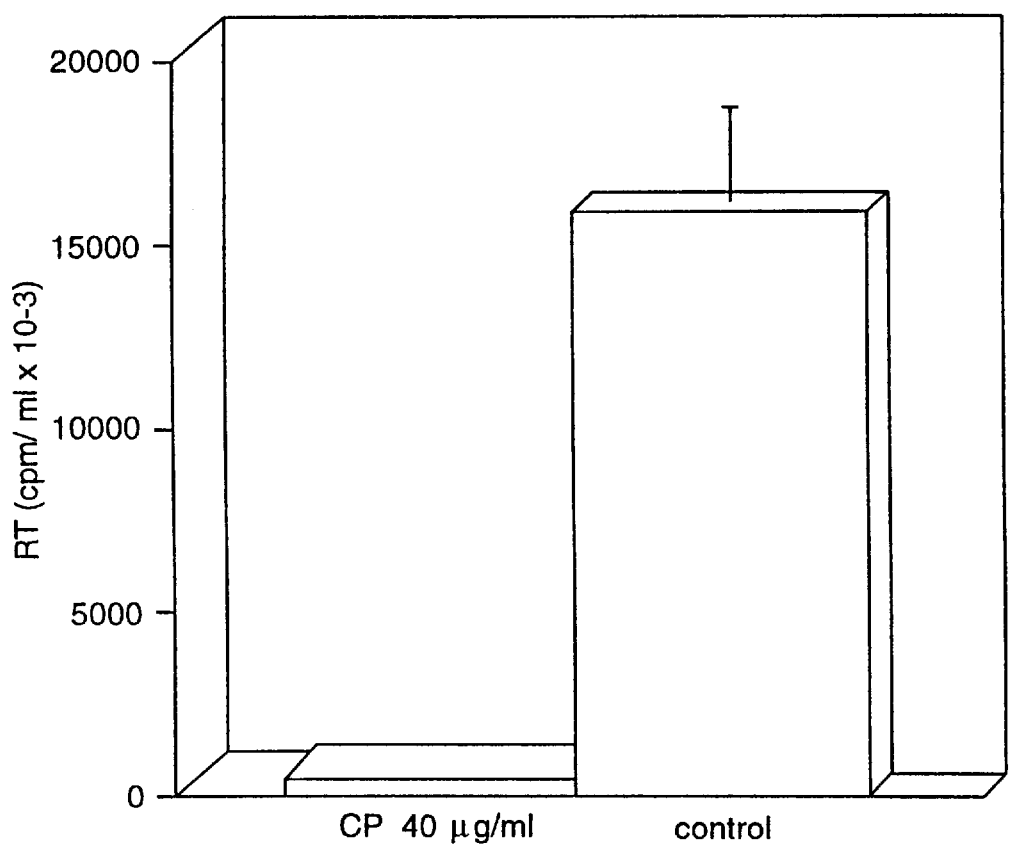

United States Patent [19]
Bukrinsky et al.

[11] Patent Number: 5,840,305
[45] Date of Patent: Nov. 24, 1998

[54] TREATMENT OF HIV-INFECTION BY INTERFERING WITH HOST CELL CYCLOPHILIN RECEPTOR ACTIVITY

[75] Inventors: Michael Bukrinsky, Glenwood Landing; Barbara A. Sherry, New York, both of N.Y.; Peter C. Ulrich, Old Tappan, N.J.; Anthony Cerami, Shelter Island, N.Y.

[73] Assignee: The Picower Institute for Medical Research, Manhasset, N.Y.

[21] Appl. No.: 615,933

[22] Filed: Mar. 14, 1996

[51] Int. Cl.⁶ .......................... A61K 39/395; C07K 16/28
[52] U.S. Cl. ...................... 424/152.1; 424/133.1; 424/144.1; 424/154.1; 424/130.1; 530/388.25
[58] Field of Search .............................. 424/133.1, 130.1, 424/144.1, 152.1, 154.1; 530/388.25

[56] References Cited

PUBLICATIONS

Burnham Am. J. Hosp. Pharm. 51:210, 1994.
Fahey et al. Clin. Exp. Immunol. 88:1, 1992.

*Primary Examiner*—Thomas M. Cunningham
*Assistant Examiner*—Martha Lubet
*Attorney, Agent, or Firm*—Jeffrey B. Oster

[57] ABSTRACT

The present invention relates to therapeutic modalities and pharmaceutical compositions for the treatment of HIV-infection using cyclophilin A and its corresponding human cellular binding partner or receptor as a target for intervention. The present invention relates to the use of exogenous or engrafted sources of cyclophilins, anti-cyclophilin antibodies, cyclophilin decoys, soluble forms of cyclophilin-binding partners and small molecules which are supplied extracellularly, and act presumably by interrupting the binding of cyclophilin A with its cellular binding partner(s) or receptor(s) as a treatment for HIV-infection. The present invention further relates to the use of forms of cyclosporin A that have been derivatized by bulky or charged substituents to inhibit cellular uptake and minimize their immunosuppressive activities, which presumably act to disrupt cyclophilin binding to its cellular receptor, likewise as a treatment for HIV-infection. The present invention further relates to genetic constructs to interfere with production and release of cyclophilin and its cognate cellular binding partner(s), to treat HIV-infection. The present invention further relates to screening assays for the identification of compounds which inhibit the interaction of cyclophilin and its cellular receptor.

4 Claims, 4 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

C C A T G G T C A A   C C C C A C C        1 7

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

A C G C T C T C C T   G A G C T A C A G A        2 0

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:3:

GAAGCTCTAT TAGATACAGG                                                                 20

(2) INFORMATION FOR SEQ ID NO:4:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (iv) ANTI-SENSE: YES (xi) SEQUENCE DESCRIPTION: SEQ ID NO:4:

TCCTGGCTTT AATTTTACTG G                                                               21

(2) INFORMATION FOR SEQ ID NO:5:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:5:

GGAATTGGAG GTTTATCAAA GT                                                              22

TREATMENT OF HIV-INFECTION BY INTERFERING WITH HOST CELL CYCLOPHILIN RECEPTOR ACTIVITY

1. INTRODUCTION

The present invention relates to therapeutic modalities and pharmaceutical compositions for the treatment of HIV-infection using cyclophilin A and its corresponding human cellular binding partner or receptor as a target for intervention. The present invention relates to the use of exogenous or engrafted sources of cyclophilins, anti-cyclophilin antibodies, cyclophilin decoys, soluble forms of cyclophilin-binding partners and small molecules which are supplied extracellularly, and act presumably by interrupting the binding of cyclophilin A with its cellular binding partner(s) or receptor(s), as a treatment for HIV-infection. The present invention further relates to a treatment for HIV-infection using forms of cyclosporin A that have been derivatized by bulky or charged substituents to inhibit cellular uptake and minimize their immunosuppressive activities, which presumably act to disrupt cyclophilin binding to its cellular receptor. The present invention further relates to genetic constructs designed to interfere with production and release of cyclophilin and its cognate cellular binding partner(s), which can be used to treat HIV-infection. The present invention further relates to screening assays for the identification of compounds which inhibit the interaction of cyclophilin and its cellular receptor.

2. BACKGROUND OF THE INVENTION
2.1. THE HUMAN IMMUNODEFICIENCY VIRUS

The human immunodeficiency virus (HIV) has been implicated as the primary cause of the slowly degenerative immune system disease termed acquired immune deficiency syndrome (AIDS) (Barre-Sinoussi, F. et al., 1983, Science 220:868–870; Gallo, R. et al., 1984, Science 224:500–503). There are at least two distinct types of HIV: HIV-1 (Barre-Sinoussi, F. et al., 1983, Science 220:868–870; Gallo R. et al., 1984, Science 224:500–503) and HIV-2 (Clavel, F. et al., 1986, Science 233:343–346; Guyader, M. et al., 1987, Nature 326:662–669). Further, a large amount of genetic heterogeneity exists within populations of each of these types. In humans, HIV replication occurs prominently in $CD4^+$ T lymphocyte populations, and HIV infection leads to depletion of this cell type and eventually to immune incompetence, opportunistic infections, neurological dysfunctions, neoplastic growth, and ultimately death.

HIV is a member of the lentivirus family of retroviruses (Teich, N. et al., 1984, RNA Tumor Viruses, Weiss, R. et al., eds., CSH-Press, pp. 949–956). Retroviruses are small enveloped viruses that contain a single-stranded RNA genome, and replicate via a DNA intermediate produced by a virally-encoded reverse transcriptase, an RNA-dependent DNA polymerase (Varmus, H., 1988, Science 240:1427–1439). Other retroviruses include, for example, oncogenic viruses such as human T cell leukemia viruses (HTLV-I,-II,-III), and feline leukemia virus.

The HIV viral particle comprises a viral core, composed in part of capsid proteins, together with the viral RNA genome and those enzymes required for early replicative events. Myristylated Gag protein forms an outer shell around the viral core, which is, in turn, surrounded by a lipid membrane envelope derived from the infected cell membrane. The HIV envelope surface glycoproteins are synthesized as a single 160 Kd precursor protein which is cleaved by a cellular protease during viral budding into two glycoproteins, gp41 and gp120. gp41 is a transmembrane glycoprotein and gp120 is an extracellular glycoprotein which remains non-covalently associated with gp41, possibly in a trimeric or multimeric form (Hammarskjold, M. and Rekosh, D., 1989, Biochem. Biophys. Acta 989:269–280).

HIV is targeted to $CD4^+$ cells because a CD4 cell surface protein (CD4) acts as the cellular receptor for the HIV-1 virus (Dalgleish, A. et al., 1984, Nature 312:763–767; Klatzmann et al., 1984, Nature 312:767–768; Maddon et al., 1986, Cell 47:333–348). Viral entry into cells is dependent upon gp120 binding the cellular CD4 receptor molecules (McDougal, J. S. et al., 1986, Science 231:382–385; Maddon, P. J. et al., 1986, Cell 47:333–348), explaining HIV's tropism for $CD4^+$ cells, while gp41 anchors the envelope glycoprotein complex in the viral membrane. While these virus:cell interactions are necessary for infection, there is evidence that additional virus:cell interactions are also required.

2.2. HIV TREATMENT

HIV infection is pandemic and HIV-associated diseases represent a major world health problem. Although considerable effort is being put into the design of effective therapeutics, currently no curative anti-retroviral drugs against AIDS exist. In attempts to develop such drugs, several stages of the HIV life cycle have been considered as targets for therapeutic intervention (Mitsuya, H. et al., 1991, FASEB J. 5:2369–2381). For example, virally encoded reverse transcriptase has been one focus of drug development. A number of reverse-transcriptase-targeted drugs, including 2', 3'-dideoxynucleoside analogs such as AZT, ddI, ddC, and d4T have been developed which have been shown to been active against HIV (Mitsuya, H. et al., 1991, Science 249:1533–1544). While beneficial, these nucleoside analogs are not curative, probably due to the rapid appearance of drug resistant HIV mutants (Lander, B. et al., 1989, Science 243:1731–1734). In addition, the drugs often cause toxic side effects such as bone marrow suppression, vomiting, and liver function abnormalities.

Attempts are also being made to develop drugs which can inhibit viral entry into the cell, the earliest stage of HIV infection. Here, the focus has thus far been on CD4, the cell surface receptor for HIV. Recombinant soluble CD4, for example, has been shown to inhibit infection of $CD4^+$ T cells by some HIV-1 strains (Smith, D. H. et al., 1987, Science 238:1704–1707). Certain primary HIV-1 isolates, however, are relatively less sensitive to inhibition by recombinant CD4 (Daar, E. et al., 1990, Proc. Natl. Acad. Sci. USA 87:6574–6579). In addition, recombinant soluble CD4 clinical trials have produced inconclusive results (Schooley, R. et al., 1990, Ann. Int. Med. 112:247–253; Kahn, J. O. et al., 1990, Ann. Int. Med. 112:254–261; Yarchoan, R. et al., 1989, Proc. Vth Int. Conf. on AIDS, p. 564, MCP 137).

The late stages of HIV replication, which involve crucial virus-specific processing of certain viral encoded proteins, have also been suggested as possible anti-HIV drug targets. Late stage processing is dependent on the activity of a viral protease, and drugs are being developed which inhibit this protease (Erickson, J., 1990, Science 249:527–533). The clinical outcome of these candidate drugs is still in question.

Attention is also being given to the development of vaccines for the treatment of HIV infection. The HIV-1 envelope proteins (gp160, gp120, gp41) have been shown to be the major antigens for anti-HIV antibodies present in AIDS patients (Barin, et al., 1985, Science 228:1094–1096). Thus far, therefore, these proteins seem to be the most promising candidates to act as antigens for anti-HIV vaccine development. Several groups have begun to use various portions of gp160, gp120, and/or gp41 as immunogenic targets for the host immune system. See for example, Ivanoff, L. et al., U.S. Pat. No. 5,141,867; Saith, G. et al., WO 92/22,654; Shafferman, A., WO 91/09,872; Formoso, C. et al., WO 90/07,119. To this end, vaccines directed against HIV proteins are problematic in that the virus mutates rapidly rendering many of these vaccines ineffective. Clinical results concerning these candidate vaccines, however, still remain far in the future.

Thus, although a great deal of effort is being directed to the design and testing of anti-retroviral drugs, effective, non-toxic treatments are still needed.

2.3. CYCLOPHILIN

Cyclophilin A is a 19 KD protein, which is abundantly expressed in a wide variety of cells. Cyclophilin A binds the immunosuppressive agent, cyclosporin A, and possesses peptidyl-prolyl cis-trans isomerase (PPIase), and protein folding or "chaperone" activities. Cyclophilin A is a member of the "immunophilin family", i.e., a group of related cellular factors involved in regulating immunity. At least four types of mammalian cyclophilins have been cloned, cyclophilins A, B, C and hCyP3 (Friedman et al., 1993, Proc. Natl. Acad. Sci., 90:6815–6819). A glycoprotein with a N-terminal signal sequence has been identified which binds cyclophilin C, but not cyclophilin A or B (Friedman et al., supra). The functional significance of this interaction has yet to be elucidated. A homologous protein was found in mouse macrophages, MAC-2 binding protein, and is postulated to be involved in the cascade of immunoregulatory events resulting from the absorption of the immunosuppressive drug cyclosporin A (Chicheportiche et al., 1994, Proc. Natl. Acad. Sci., 269:5512–5577).

Very recently, a functional association of cyclophilin A with the Gag protein of HIV virions and specifically with the capsid antigen portion thereof, was noted (Thali et al., 1994, Nature 372:363–365). Cyclophilin was reported to be specifically incorporated into HIV-1 virions, and disruption of the Gag-cyclophilin interaction was reported to prevent both incorporation of cyclophilin A into virions and HIV-1 replication, indicating that the interaction of Gag with cyclophilin A is necessary for the formation of infectious HIV-1 virions (Franke et al., 1995, Nature 372:359–362; Thali et al., 1994, Nature 372:363–365).

Cyclophilin is recognized to be one of the host cell receptors for cyclosporin A—a potent immunosuppressive drug which is widely used in prevention of graft rejection. Cyclosporin A is a member of a family of hydrophobic cyclic undecapeptides that exhibits potent immunosuppressive, antiparasitic, fungicidal and chronic anti-inflammatory properties. Cyclosporin A is thought to exert its immunosuppressive effects by inhibiting the early stages in T cell activation. Cyclosporin A has been found to block RNA transcription of the T cell growth factor, interleukin 2 (IL-2) and to inhibit expression of the IL2 receptor by precursor cytolytic T lymphocytes (Palacios, 1982, J. Immunol. 128:337). Cyclophilin A is thought to be responsible for the cell type specific activities of cyclosporin A in lymphoid cells, through the interaction of the cyclosporin A:cyclophilin complex with the cellular factor calcineurin, a calcium-dependent serine/threonine phosphatase. Cyclophilin A binds to cyclosporin A with a dissociation constant in the range of $10^{-8}$ mol/L, a value consistent with levels needed to elicit immunosuppression (Handschumacher et al., 1984, Science 226:544).

Cyclosporin A and certain of its non-immunosuppressive analogs have been shown to interfere with Gag-cyclophilin interactions in vitro, block cyclophilin incorporation into virions, and inhibit the replication of HIV-1 in cell culture (Franke et al., supra; Thali et al., supra; Billich et al., 1995, J. Virol. 69:2451–2461). Cyclosporin A has not been shown to interact directly with the HIV-1 virus. The interaction of HIV Gag with cyclophilin A, and the inhibition of viral replication by cyclosporin A is not observed for related retroviruses, such as simian immunodeficiency virus (SIV). (Franke et al. supra; Billich et al. supra). It is hypothesized that cyclosporin A, and its analogs, interfere at two stages in the HIV life cycle by interacting with cyclophilin A—during establishment of infection where cyclosporin A treatment inhibits HIV infection prior to integration into the genome of the infected cell as measured by formation of circular HIV DNA and integration of proviral DNA into the host genome; and at a late stage of virus replication, when a reduction in shed virus particles but not viral antigen expression is observed (Billich et al., supra). Therefore, researchers have been focused on disrupting the interaction between the viral protein, Gag, and the cellular protein, cyclophilin A, in their attempts to develop an anti-HIV agent.

Despite the foregoing observations, the usefulness of cyclosporin A as a treatment for HIV-infection in patients is severely limited. First, cyclosporin A is a potent immunosuppressor, therefore its use in HIV-infected patients, who will become immunocompromised, is contraindicated. Moreover, the noted HIV-inhibitory effects of cyclosporin A and its analogs required drug concentrations that are 10 to 100-fold higher than those necessary to effectuate immunosuppression with cyclosporin A.

The ability of cyclosporin to generally suppress the systemic immune system has been proposed as a treatment for HIV infection (see U.S. Pat. No. 4,814,323). This method of treatment however has severe drawbacks, given the severely immunosuppressed state of HIV-infected patients.

Despite its limitations, researchers have speculated that cyclosporin A might be used as a treatment for HIV infection. Cyclosporin derivatives that are reported to be devoid of immunosuppressive activity but retain binding capacity for cyclophilin A and inhibit HIV in vitro, have been described. An example is the analog of cyclosporin A, SD2 N1M811, in which the N-methyl-L-leucine unit at position 4 of cyclosporin A is replaced by N-methyl-L-isoleucine. (Traber et al., 1994, Antiviral Chemistry & Chemotherapy, 5:331–339). This cyclosporin analog is reported to be devoid of immunosuppressive activity, but retains full capacity to bind to cyclophilin and exhibit anti-HIV-1 infection activity in vitro as measured by cytopathic effects and particle production. Other derivatized cyclosporin analogs include novel cyclosporin derivatives modified at positions 4 and 5 of cyclosporin A. (EP 484 281, Feb. 24, 1993). Additional immunosuppressive cyclosporin analogs have been developed which consist of cyclosporins with sulfur containing amino acids at position 8. (EP 444 897, Sep. 4, 1991). These cyclosporin derivatives are able to enter the cell, and are thought to mediate their effects intracellularly, after the HIV virus has entered the cell, by targeting the cyclophilin A and HIV-Gag interaction.

Many researchers now seek to develop drugs which target the interaction between cyclophilin A and Gag in order to disrupt the HIV life cycle (Sternberg, 1996, BioWord Today 7:1).

3. SUMMARY OF THE INVENTION

The present invention relates to therapeutic modalities and pharmaceutical compositions for the treatment of HIV-infection directed to the interaction between cyclophilin A and its cell receptor(s) or binding partner(s) as a target for intervention. The present invention further relates to screening assays to identify compounds and compositions effective against HIV infection by inhibiting the interaction between cyclophilin and its cell receptor(s) or binding partner(s).

The invention is based, in part, on the Applicants' discovery that an extracellularly supplied cyclophilin, or neutralizing antibody for cyclophilin A, as well as cyclosporin A derivatives modified to inhibit their internalization by host cells, each inhibit HIV replication. This discovery is described in working examples presented infra, which demonstrate that exogenous cyclophilin A, an extracellularly supplied neutralizing antibody for cyclophilin A, and an extracellularly supplied cyclosporin A derivative modified so as to be excluded from cell entry, each inhibit HIV replication. This result is surprising since cyclophilin A, a cellular protein having immunomodulatory activity, is believed to be incorporated into HIV virions by binding to HIV-Gag and is thought to be required for productive viral infection (e.g., viral assembly and transmission) since, although certain cyclosporins have demonstrated efficacy against HIV infection in cellular host systems, these peptides have been thought to act within the infected cells. The Gag-cyclophilin A complex contained in the core of the virion is surrounded by a lipid envelope bearing HIV-envelope glycoproteins. As such, the Gag-cyclophilin complex is generally understood not to be exposed to exogenous cyclophilin, to the extracellular neutralizing antibody, or to cyclosporin A derivatized to inhibit internalization by the cells.

While not limited to any theory or explanation, the Applicants' novel hypothesis is that a host cell binding factor for cyclophilin A exists, and its interaction with virus-associated cyclophilin is required, in addition to host CD4 receptor interaction, for efficient infection of CD4+ host cells by HIV, (e.g., attachment, uncoating and nuclear translocation). That a host cell receptor or binding partner for cyclophilin A is involved in HIV-infection is further supported by the working examples described infra which demonstrate that exogenous cyclophilin A inhibits HIV-infection. Presumably, the exogenous cyclophilin occupies or competes with HIV-virion-associated cyclophilin for the cellular cyclophilin binding partner or receptor.

The various modalities of treatment described herein were designed on the basis of the proposed model. In particular, any compound or composition which interferes with the interaction of cyclophilin and its cellular receptor or binding partner to inhibit HIV-infection is encompassed by the present invention. The focus of the anti-HIV treatment of the present invention is to prevent viral infection (e.g., attachment, uncoating and translocation to the host cell nucleus) as opposed to inhibiting an ongoing viral infection (e.g., viral assembly and budding). The present invention relates to the use of an exogenous or engrafted source of cyclophilin, anti-cyclophilin antibodies, cyclophilin decoys, soluble forms of cyclophilin binding proteins, and small molecules which act presumably by interrupting the binding of cyclophilin with its cellular binding partner(s) or receptor (s).

In particular, antibodies that neutralize cyclophilin can be used to inhibit HIV infection. In one embodiment of the present invention, neutralizing antibodies which have been generated outside the patient to be treated, for instance using cyclophilin as an antigen, can be administered in a passive immunotherapy approach. In a preferred embodiment, cyclophilin is used in conjunction with an adjuvant and is covalently modified, as by glycation, to improve antigenicity and the utility of the antibodies. In another embodiment of the present invention, cyclophilin can be formulated as an immunogen, for instance in conjunction with an adjuvant, for use as a "vaccine" to generate an active immune response in HIV-infected patients. In a preferred embodiment, cyclophilin is modified by advanced glycation to improve immunogenicity or to improve the characteristics of the elicited antibodies for the intended purposes.

Cyclosporins, which would ordinarily result in immunosuppression due to their intracellular interaction with cyclophilin A, can be derivatized to inhibit the entry of the drug into cells, for instance by the covalent attachment of bulky or charged substituents and thereby to render these derivatives non-immunosuppressive. In a preferred embodiment, a cyclosporin is modified by attachment of polyethylene glycol substituents. Such cyclosporin derivatives can be used to inhibit HIV-infection without inducing immunosuppression in HIV-infected patients.

The present invention further relates to the use of exogenous cyclophilin to interfere with HIV-infection, and to the use of cyclophilin derivatives that are unable to form complexes with HIV-Gag, yet are still able to bind the cyclophilin host receptor. Therefore, these cyclophilin derivatives are unable to be incorporated into virions, yet compete with or block the binding of the HIV-virion-associated cyclophilin to host binding proteins.

The present invention still further relates to various recombinant DNA and cellular engraftment or gene therapy strategies to increase cyclophilin expression and release from adjunct cell populations or to inhibit expression of cyclophilin or cyclophilin binding proteins in cells susceptible to HIV-infection.

3.1. DEFINITIONS

Cyclophilin (CyP) as used herein refers to the protein cyclophilin of which four types are known, CyPA, CyPB, CyPC and hCyP3, which is the receptor for cyclosporin A, and any derivative of cyclophilin thereof, or fragments or peptides having an amino acid sequence corresponding to cyclophilin.

Cyclosporin (CsA) as used herein refers to the immunosuppressive drug, cyclosporin, and any derivative of cyclosporin thereof, or fragments or peptides having an amino acid sequence corresponding to cyclosporin.

Cyclophilin binding partner as used herein means any cellular binding protein, cell surface binding protein, extracellular receptor, or intracellular binding protein, which has cyclophilin specific binding activity.

4. BRIEF DESCRIPTION OF THE DRAWINGS

FIG. 1. Inhibition of HIV-1 infection in H9 cell cultures treated with exogenous cyclophilin at 40 μg/ml. As an index of the extent of HIV-1 infection, reverse transcriptase (RT) activity was assayed in culture supernatants 5 days post-infection, according to standard methods.

FIG. 2. Inhibition of HIV-1 infection in H9 cell cultures treated with exogenous cyclophilin (at 1 or 40 μg/ml) or with whole antiserum to glycated cyclophilin (α-AGE-CyP) or to non-modified cyclophilin (α-CyP). As an index of the extent of HIV-1 infection, reverse transcriptase (RT) activity was assayed in culture supernatants 3 days post-infection, according to standard methods.

FIG. 3. Time course of inhibition of HIV-1 infection in human PBL cultures treated with exogenous cyclophilin at 40 μg/ml. As an index of the extent of HIV infection, p24 antigen levels in culture supernatants were assayed by a commercially available ELISA.

FIG. 4. Inhibition of HIV-1 infection in human monocyte/macrophage cultures by cyclophilin, anti-cyclophilin antibodies, and cyclosporin A derivatized to inhibit cell entry. Inhibition was assessed as the percent inhibition of HIV pol retrotranscription measured in quantitative PCR assays by reference to appropriate controls.

5. DETAILED DESCRIPTION OF THE INVENTION

The present invention relates to therapeutic modalities and pharmaceutical compositions for the treatment of HIV-infection; these agents are designed to interfere with the interaction between cyclophilin A and cellular binding proteins specific for cyclophilin A. A variety of techniques and compositions may be utilized to inhibit the interaction of cyclophilin A and its specific binding partner(s), thereby inhibiting HIV-infection.

In a first embodiment of the present invention, cyclophilin can be administered to inhibit HIV infection in patients. This cyclophilin may be a protein having a sequence substantially identical to human cyclophilin A, B or C, or to a cyclophilin of another species (i.e., mouse, yeast) or the protein may be a mutant of any of the above native sequences. When administered in accordance with the present invention such treatment will have utility as an anti-HIV-infection treatment, by interfering with the interaction between virus-associated cyclophilin and host cell proteins.

In an additional embodiment of the present invention, neutralizing antibodies which have been generated against cyclophilin can be administered in a passive immunotherapy approach. The present invention also relates to the use of cyclophilin formulated as an immunogen. The use of cyclophilin as a "vaccine" will generate an active immune response useful in HIV-infected patients. In a preferred embodiment, cyclophilin for use as an immunogen is first modified by non-enzymatic glycosylation to improve antigenicity or the desired properties of the antigen-specific immune response.

Another embodiment of the present invention are the small organic molecules that interfere with the interaction of virus-associated cyclophilin and host cell proteins to inhibit HIV infection. Such small molecules useful in this regard are cyclosporins, which would ordinarily result in immunosuppression due to their interaction with intracellular cyclophilin A, but which are derivatized so as to inhibit their entry into cells, for instance by the covalent attachment of bulky or charged substituents, such as polyethylene glycol. The extracellularly presented cyclosporin derivatives can be used to inhibit HIV-infection; this is thought to be attributable to blocking the interaction between cyclophilin A and its cellular binding proteins, particularly such binding proteins as are accessible to extracellularly presented derivatized cyclosporins, which by their modification are without significant immunosuppressive activity.

In a further embodiment, cyclophilin is derivatized or mutated so that it is unable to form a complex with Gag, yet is still capable of binding to cellular cyclophilin binding proteins. Such cyclophilin derivatives, while not incorporated into virions, are able to compete with or block the binding of cyclophilin-specific binding proteins to HIV viral components, such as Gag.

The present invention additionally relates to screening assays to identify compounds which inhibit HIV infection, these compounds are selected for their activity in blocking the interaction between cyclophilin A and its cellular binding proteins. Such identified compounds would have utility in the treatment and prevention of HIV-infection.

5.1. THE ROLE OF CYCLOPHILIN A AND ITS HOST CELL RECEPTOR IN HIV-INFECTION

The present invention is based, in part, on the Applicants' surprising discovery that, when provided extracellularly, exogenous cyclophilin A, a neutralizing antibody for cyclophilin A, and cyclosporin A derivatives, which are modified to inhibit their entry into host cells, each inhibit HIV replication and infection in cell culture. This discovery is exemplified in Sections 6 and 7 infra, which demonstrate that extracellularly supplied cyclophilin A or neutralizing antibodies for cyclophilin A, which are generally thought not to be internalized by host cells, are capable of inhibiting HIV replication. The examples in Sections 6 and 7 infra also demonstrate that an extracellularly supplied cyclosporin A, modified so as to be excluded from cell entry and therefore a nonimmunosuppressive derivative, inhibits HIV-replication. These results are surprising since the only known HIV-infection related molecular interaction with cyclophilin, the Gag-cyclophilin A complex, is contained in the core of the HIV virion, which is surrounded by a lipid envelope bearing the HIV-envelope glycoproteins. As such, the Gag-cyclophilin complex should not be exposed to the extracellularly supplied cyclophilin A, neutralizing antibody or derivatized cyclosporin A. While not limited to any theory or explanation, the Applicants' novel hypothesis, that a host cell binding factor or receptor for cyclophilin exists, and is required in addition to the host CD4 receptor, for efficient infection of CD4+ host cells by HIV (e.g., attachment, uncoating and translocation to the nucleus), was developed.

That a host cell binding activity specific for cyclophilin A is involved in HIV-infection is further supported by the working examples described infra which demonstrate that exogenous cyclophilin A inhibits HIV-infection.

As discussed above, the Applicants' work shows that inhibition of cyclophilin-specific binding interactions by extracellularly presented antagonists is effective in inhibiting cellular infection by HIV. A variety of techniques and compositions may be utilized to inhibit the interaction of cyclophilin with its corresponding cellular binding partner or receptor, thereby inhibiting HIV infection.

For example, compounds which may be used in accordance with the present invention encompass any compound which interferes with the interaction between cyclophilin and its cellular binding partner or receptor, including, but not limited to neutralizing antibodies against cyclophilin and the use of cyclophilin as an immunogen to generate an active immune response in HIV-infected patients. Other examples of compounds which may be used in accordance with the present invention include cyclophilin A and advantageously nonimmunosuppressive derivatives of cyclosporin which inhibit the interaction between virus-associated cyclophilin A and its cellular binding partner(s) or receptor(s) and correspondingly inhibit HIV infection. Other examples of compounds which may be used in accordance with the present invention include, but are not limited to, peptides (such as, for example, peptides representing soluble portions of cyclophilin binding partner or receptor), phosphopeptides, small organic or inorganic molecules, or antibodies (including, for example, polyclonal, monoclonal, humanized, anti-idiotypic, chimeric or single chain antibodies, and FAb, F(ab')$_2$ and FAb expression library fragments, and epitope-binding fragments thereof). Techniques for determination of effective doses and administration of such compounds are described below, in Section 5.7 infra.

In addition, expression vectors and genetic constructs providing the expression and release of cyclophilin and various useful mutant proteins corresponding thereto and identified by the teachings of the present invention, or of a cyclophilin-binding partner or a cyclophilin-binding domain thereof, as well as the cells harboring such vectors and constructs are also useful in accordance with the invention.

Further, antisense and ribozyme molecules which inhibit expression of the target gene, that is cyclophilin or its cellular binding partner or receptor, may also be used in accordance with the invention to inhibit HIV infection by interfering with the interaction between the cyclophilin and its cellular binding partner or receptor.

In addition, compounds such as those identified through the screening assays described in Section 5.6 infra may also be used in accordance with the present invention.

5.2. ANTI-CYCLOPHILIN ANTIBODIES

The present invention relates to the use of neutralizing antibodies against cyclophilin, optionally raised against derivatized cyclophilin, in a passive immunotherapy approach and the use of cyclophilin, optionally a derivatized form of cyclophilin, as an immunogen to generate an active immune response in HIV-infected patients.

5.2.1. PASSIVE IMMUNOTHERAPY APPROACH

The present invention relates to the use of neutralizing antibodies which interact with cyclophilin, or with its cellular binding partner, and inhibit HIV infection. By way of explanation, but without being limited to any theory, Applicants propose that such antibodies disrupt the interaction between cyclophilin and its host cellular binding partner or receptor thereby inhibiting HIV-infection. These neutralizing antibodies of the invention can be administered in a passive immunotherapy approach. In a preferred embodiment of the invention, the neutralizing antibodies are generated using glycated cyclophilin. Methods for glycating cyclophilin are described in WO 93/23081 which is incorporated herein in its entirety by reference.

Antibodies that are specific for cyclophilin A or its host cellular binding partner or receptor may be generated to inhibit HIV-infection, and these antibodies are thought to work in this regard by interfering with the interaction between virally-associated cyclophilin and its cellular binding partner or receptor. For passive immunotherapy approaches, such antibodies may be generated using standard techniques known to those skilled in the art against the proteins themselves or against peptides corresponding to portions of the proteins. The antibodies include but are not limited to polyclonal, monoclonal, Fab fragments, single chain antibodies, chimeric antibodies, human antibodies, non-human antibodies or humanized antibodies, etc.

Where fragments of the antibody are used, the smallest inhibitory fragment which binds to the target protein's binding domain is preferred. For example, peptides having an amino acid sequence corresponding to the domain of the variable region of the antibody that binds to the target protein may be used. Such peptides can be synthesized chemically or produced via recombinant DNA technology using methods well known in the art (e.g., see Creighton, 1983, supra; and Sambrook et al., 1989, supra).

Alternatively, single chain neutralizing antibodies which bind to intracellular target epitopes may also be administered. Such single chain antibodies may be administered, for example, by expressing nucleotide sequences encoding single-chain antibodies within the target cell population by utilizing, for example, techniques such as those described in Marasco et al. (Marasco, W. et al., 1993, Proc. Natl. Acad. Sci. USA 90:7889–7893).

For the production of antibodies, various host animals may be immunized by injection with the protein, including but not limited to rabbits, mice, rats, etc. Various adjuvants may be used to increase the immunological response, depending on the host species, including but not limited to modification of the antigen of interest by the process of advanced glycation or by advanced glycation products, or by administration of the antigen with Freund's adjuvant (complete and incomplete), mineral gels such as aluminum hydroxide, surface active substances such as lysolecithin, pluronic polyols, polyanions, peptides, oil emersions, key hole limpet hemocyanin, dinitrophenol, and potentially useful human adjuvants such as BCG (bacille Calmette-Guerin) and Corynebacterium parvum.

Many methods may be used to introduce the passive vaccine formulations described above, these include but are not limited to oral, intradermal, intramuscular, intraperitoneal, intravenous, subcutaneous, and intranasal routes. It may be preferable to introduce the vaccine formulation via the natural route of infection of the pathogen for which the vaccine is designed, or into the tissue where the pathogen resides within the body.

In immunization procedures, the amount of immunogen to be used and the immunization schedule will be determined by a physician skilled in the art and will be administered by reference to the immune response and antibody titers of the subject.

5.2.2. ACTIVE IMMUNOTHERAPY APPROACH

The present invention further relates to the use of cyclophilin formulated as an immunogen and used as a "vaccine" to generate an active immune response in HIV-infected patients that are not severely immunocompromised or in populations at risk for HIV exposure and infection. In a preferred embodiment, active immunization comprises reacting the immunogen, cyclophilin, with glucose or another reducing sugar under conditions which lead to the formulation of irreversible covalent adducts, known as Advanced Glycation Endproducts (AGEs). Methods for glycating cyclophilin are described in WO 93/23081 which is incorporated herein in its entirety by reference.

An active immune response generated against cyclophilin A, or a cellular binding partner or receptor therefore, which interferes with the interaction between cyclophilin and its cellular binding partner, may be generated to inhibit HIV-infection. For active immunization, a vaccine comprising an immunogen consisting of cyclophilin or its cellular binding partner or receptor, or fragments or peptides having an amino acid sequence corresponding to the domains required for cyclophilin binding to its cellular binding partner or receptor, may be utilized to generate an immune response in the HIV patient or a person at risk for HIV exposure. These immunogens optionally may be modified by advanced glycation or advanced glycation products and may be formulated with an adjuvant to increase the immunological response, such as potentially useful human adjuvants, i.e., BCG (bacille Calmette-Guerin) and Corynebacterium parvum.

Many methods may be used to introduce the vaccine formulations described above, these include but are not limited to oral, intradermal, intramuscular, intraperitoneal, intravenous, subcutaneous, and intranasal routes. It may be preferable to introduce the vaccine formulation via the natural route of infection of the pathogen for which the vaccine is designed.

In immunization procedures, the amount of immunogen to be used and the immunization schedule will be determined by a physician skilled in the art and will be administered by reference to the immune response and antibody titers of the subject.

5.3. CYCLOSPORIN DERIVATIVES

The present invention encompasses cyclosporin derivatives that are modified so as to inhibit their entry into or internalization by host cells, such that the derivatives of cyclosporin are correspondingly not interactive with intracellular cyclophilin A. Such cyclosporin derivatives of the present invention are believed to act to inhibit HIV viral entry when presented extracellularly. Such cyclosporin derivatives should inhibit infection by HIV, yet should not result in immunosuppression of the HIV-infected patient. Therefore, the invention encompasses derivatives of cyclosporin which prevent or minimize internalization of the molecule by the cell, yet do not prevent interaction with the cyclophilin, thereby inhibiting HIV-infection. Cyclosporin may be derivatized by the addition of a bulky substituent to the protein. Examples of such substituents, include but are not limited to, charged substituents (e.g., spermine or spermidine), polynucleotides with and without modified backbones, carbohydrates (e.g., polyacrylic acid, polysodium acrylate, polycesium acrylate, polymethacrylic acid), amphiphilic block copolymers (e.g., polystyrene poly) (sodium acrylate), and amphiphilic homopolymers.

In a preferred embodiment of the invention, cyclosporin is derivatized by reaction with polyethylene glycol, resulting in a "pegylated" cyclosporin. Pegylated cyclosporin may be prepared by standard chemical methods known to those skilled in the art. The preferred method of preparing the pegylated cyclosporin of the invention, involves reacting methoxypolyethylene glycol-succinimidyl succinate with 8-amino-cyclosporin A and 4-dimethylamino pyridine in methylene chloride with stirring for two days at room temperature in the dark. To block any unreacted sites, ethanolamine was then added and the mixture incubated at room temperature with stirring for another 24 hours. The derivatized cyclosporin A is purified from the reaction mixture by normal phase HPLC.

5.4. CYCLOPHILIN AND CYCLOPHILIN BINDING PARTNER DERIVATIVES

Another embodiment of the invention relates to the use of exogenous cyclophilin to inhibit the interaction between cyclophilin and its cellular binding partner or receptor. Examples of exogenous forms of cyclophilin include but are not limited to human cyclophilin A, other human cyclophilins, the cyclophilins of other species (i.e., mouse, yeast) derivatized cyclophilin, recombinant cyclophilin, cyclophilin fusion proteins or peptide fragments expressing the domain of cyclophilin which binds to its host cell receptor. The present invention relates both to forms of cyclophilin which do and do not form complexes with the Gag protein, and therefore are not incorporated by the HIV virion, yet bind to the host cell cyclophilin binding partner or receptor and therefore, block binding of the Gag-cyclophilin complex.

A further embodiment of the invention relates to the use of exogenous cyclophilin binding protein(s) to inhibit the interaction between cyclophilin and its cellular binding partner. Examples of exogenous forms of cyclophilin binding partners or receptors include but are not limited to derivatized cyclophilin binding partners, recombinant cyclophilin binding partners, fusion proteins or peptide fragments expressing the domain of the cyclophilin binding partner or receptor which binds to cyclophilin.

In a further embodiment of the present invention, a therapeutic modality for HIV-infection embodying the genetic engineering of cells to produce or release cyclophilin constitutively or in response to suitable inducers and the supply of said cells to an HIV patient by engraftment of exogenously transfected cells or treatment of the patient by gene therapy to transfect endogenous cell populations is envisioned. This therapeutic modality is likewise suitable to implement HIV treatment by expression and release of cyclophilin mutants, molecular decoys or other mimics of cyclophilin that inhibit HIV infection, for instance by interfering with the interactions between virus associated cyclophilin and such cellular binding proteins, therefore, as are required for productive infection. Therapeutic modalities capitalizing on the genetic engineering of cells to express and release soluble forms of cyclophilin-binding proteins or the cyclophilin-binding domains thereof will likewise find utility in the practice of the present invention and are contemplated hereunder.

Cyclophilin may be derivatized by a variety of methods known to those skilled in the art. In a preferred embodiment of the invention, cyclophilin is pegylated by reacting cyclophilin with methoxypolyethylene glycol-succinimidyl succinate and 4-dimethylamino pyridine in methylene chloride with stirring for two days at room temperature in the dark. To block any unreacted sites, ethanolamine is added and the mixture incubated at room temperature with stirring for another 24 hours. The pegylated cyclophilin is purified from the reaction mixture by normal phase HPLC.

The recombinant forms of cyclophilin, the fusion proteins or peptides expressing the domain of cyclophilin that binds to its cellular receptor can be produced by synthetic techniques or via recombinant DNA technology using techniques well known in the art. Thus, methods for preparing the differentially expressed cyclophilin polypeptides and peptides of the invention are described herein. First, the polypeptides and peptides of the invention can be synthesized or prepared by techniques well known in the art. See, for example, Creighton, 1983, "Proteins: Structures and Molecular Principles", W. H. Freeman and Co., N.Y., which is incorporated herein by reference in its entirety. Peptides can, for example, be synthesized on a solid support or in solution.

Alternatively, recombinant DNA methods which are well known to those skilled in the art can be used to construct expression vectors containing differentially expressed cyclophilin protein coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, Molecular Cloning: A Laboratory Manual, Cold Spring Harbor Press, Cold Spring Harbor, N.Y. which are incorporated by reference herein in their entirety, and Ausubel, 1989, supra. Alternatively, RNA capable of encoding differentially expressed cyclophilin protein sequences can be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems can be utilized to express the cyclophilin coding sequences of the invention. Such host-expression systems represent vehicles by which the coding sequences of interest can be produced and subsequently purified, but also represent cells which can, when transformed or transfected with the appropriate nucleotide coding sequences, exhibit or produce and release the cyclophilin protein of the invention in situ. These include but are not limited to microorganisms such as bacteria (e.g., *E. coli, B. subtilis*) transformed with recombinant bacteriophage DNA, plasmid DNA or cosmid DNA expression vectors containing cyclophilin protein coding sequences; yeast (e.g., Saccharomyces, Pichia) transformed with recombinant yeast expression vectors containing the cyclophilin protein coding sequences; insect cell systems infected with recombinant virus expression vectors (e.g., baculovirus) containing the cyclophilin protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing cyclophilin protein coding sequences; or mammalian cell systems (e.g. COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the cyclophilin protein being expressed. For example, when a large quantity of such a protein is to be produced, for the generation of antibodies or to screen peptide libraries, for example, vectors which direct the expression of high levels of fusion protein products that are readily purified can be desirable. Such vectors include, but are not limited, to the E. coli expression vector pUR278 (Ruther et al., 1983, EMBO J. 2:1791), in which the cyclophilin protein coding sequence can be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene protein can be released from the GST moiety.

In an insect system, Autographa californica nuclear polyhidrosis virus (ACNPV) is used as a vector to express foreign genes. The virus grows in Spodoptera frugiperda cells. The cyclophilin coding sequence can be cloned individually into non-essential regions (i.e., the polyhedrin gene) of the virus and placed under control of an AcNPV promoter (for example the polyhedrin promoter). Successful insertion of cyclophilin coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed, (e.g., see Smith et al., 1983, J. Viol. 46:584; Smith, U.S. Pat. No. 4,215,051).

In mammalian host cells, a number of expression systems, including for instance viral-based expression systems, can be utilized and either the protein expressed on the cells or the cells expressing the protein may be utilized in accordance with the present invention. In cases where an adenovirus is used as an expression vector, the cyclophilin coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing cyclophilin protein in infected hosts, (e.g., See Logan & Shenk, 1984, Proc. Natl. Acad. Sci. USA 81:3655–3659).

Specific initiation signals can also be required for efficient translation of inserted cyclophilin coding sequences. These signals include the ATG initiation codon and adjacent sequences. In cases where an entire cyclophilin gene, including its own initiation codon and adjacent sequences, is inserted into the appropriate expression vector, no additional translational control signals can be needed. However, in cases where only a portion of the cyclophilin coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see Bittner et al., 1987, Methods in Enzymol. 153:516–544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably express the cyclophilin protein can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the cyclophilin protein or a cyclophilin-binding protein. Such engineered cell lines can be particularly useful in screening and evaluation of compounds that affect the endogenous activity of the cyclophilin protein.

A number of selection systems can be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin genes (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cells lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

When used as a component in assay systems such as those described herein, the cyclophilin protein can be labeled, either directly or indirectly, to facilitate detection of a complex formed between the cyclophilin protein and a test substance. Any of a variety of suitable labeling systems can be used including but not limited to radioisotopes such as $^{125}I$; enzyme labelling systems that generate a detectable calorimetric signal or light when exposed to substrate; and fluorescent labels.

Indirect labeling involves the use of a protein, such as a labeled antibody, which specifically binds to either a cyclophilin product or a cyclophilin-binding partner product. Such antibodies include but are not limited to polyclonal, monoclonal, chimeric, single chain, Fab fragments and fragments produced by an Fab expression library.

Where recombinant DNA technology is used to produce the cyclophilin protein or a cyclophilin-binding partner, for instance for use in such assay systems, it can be advantageous to engineer fusion proteins that can facilitate labeling (either direct or indirect), immobilization, solubility and/or detection.

Fusion proteins, which can facilitate solubility and/or expression, and can increase the blood half-life of the protein, can include, but are not limited to soluble Ig-tailed fusion proteins. Methods for engineering such soluble Ig-tailed fusion proteins are well known to those of skill in the art. See, for example U.S. Pat. No. 5,116,964, which is incorporated herein by reference in its entirety. Further, in addition to the Ig-region encoded by the IgG1 vector, the Fc portion of the Ig region utilized can be modified, by amino acid substitutions, to reduce complement activation and Fc binding. (See, e.g., European Patent No. 239400 B1, Aug. 3, 1994).

These and other gene splicing and recombinant protein expression systems well known in the art are useful to produce proteins, such as cyclophilin or a cyclophilin-binding partner protein, and to produce cells that express cyclophilin or cyclophilin-binding partner proteins useful in the context of expression cell engraftment or gene therapy as described herein.

5.5. GENE THERAPY APPROACHES

Among the compounds which may disrupt the interaction of cyclophilin with its cellular binding partner or receptor are antisense, ribozyme and triple helix molecules. Such molecules are designed to inhibit expression of the target genes cyclophilin A, or its cellular binding partner or receptor in HIV-infected host cells. Techniques for the production and use of such molecules are well known to those of skill in the art.

Anti-sense RNA and DNA molecules act to directly block the translation of mRNA by hybridizing to targeted mRNA and preventing protein translation. With respect to antisense DNA, oligodeoxyribonucleotides derived from the translation initiation site, e.g., between the −10 and +10 regions of the target gene nucleotide sequence of interest, are preferred.

Ribozymes are enzymatic RNA molecules capable of catalyzing the specific cleavage of RNA. (For a review, see Rossi, J., 1994, Current Biology 4:469–471). The mechanism of ribozyme action involves sequence specific hybridization of the ribozyme molecule to complementary target RNA, followed by a endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding target gene proteins.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridize with complementary oligonucleotides, using ribonuclease protection assays.

Nucleic acid molecules to be used in triple helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and $CGC^+$ triplets across the three associated strands of the resulting triple helix. The pyrimidine-rich molecules provide base complementarily to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'–3', 3'–5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may be introduced into cells via gene therapy methods such as those described, that do not contain sequences susceptible to whatever antisense, ribozyme, or triple helix treatments are being utilized. Alternatively, in instances whereby the target gene encodes an extracellular protein, it may be preferable to coadminister normal target gene protein in order to maintain the requisite level of target gene activity.

Anti-sense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules may be introduced as a means of increasing intracellular stability and half-life. Possible modifications include but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

5.6. SCREENING ASSAYS FOR COMPOUNDS THAT INHIBIT THE INTERACTION OF CYCLOPHILIN WITH ITS CELLULAR BINDING PARTNER OR RECEPTOR

The following assays are designed to identify compounds or compositions that bind to cyclophilin A, its cellular binding partner or receptor and interfere with the interaction between cyclophilin A and its cellular receptor. Compounds may include, but are not limited to, small molecules, peptides such as, for example, soluble peptides, including but not limited to, peptides comprising portions of cyclophilin A or the cyclophilin binding domain of the cyclophilin cellular binding partner or receptor, antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules. Those compounds identified as inhibitors of the interaction between cyclophilin A and its cellular binding partner or receptor would have utility as anti-HIV agents.

The principle of the assays to identify compounds which inhibit the interaction of cyclophilin as the target gene or protein of interest and its cellular binding partner or receptor involves preparing a reaction mixture of the test compound and cyclophilin A and its host receptor or a cellular preparation comprising, in part, said cyclophilin-binding activity and for a time sufficient to allow the components to interact and bind, thus forming a complex which can be removed and/or detected. In order to test a compound for inhibitory activity, the reaction mixture is prepared in the presence and absence of the test compound. The test compound may be initially included in the reaction mixture, or may be added at a time subsequent to the addition of cyclophilin A and its cellular binding partner or receptor. Control reaction mixtures are incubated without the test compound or with a control agent. The formation of any complexes between the target gene protein and the cellular or extracellular binding partner is then detected. The formation of a complex in the control reaction, but not in the reaction mixture containing the test compound, indicates that the compound interferes with the interaction of the target gene protein and the interactive binding partner. Additionally, complex formation within reaction mixtures containing the test compound and normal target gene protein may also be compared to complex formation within reaction mixtures containing the test compound and a mutant target gene protein. This comparison may be important in those cases wherein it is desirable to identify compounds that disrupt interactions of mutant but not normal target gene proteins, to identify mutant target genes and proteins, that are themselves by virtue of their mutations useful to find their cognate binding partner(s) or receptor(s).

The assay for compounds that interfere with the interaction of the target gene products and binding partners can be conducted in a heterogeneous or homogeneous format. Heterogeneous assays involve anchoring either the target gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance; i.e., by adding the test substance to the reaction mixture prior to or simultaneously with the target gene protein and interactive cellular or extracellular binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the target gene protein or the interactive cellular or extracellular binding partner, is anchored onto a solid surface, while the non-anchored species is labeled, either directly or indirectly. In practice, microtitre plates are conveniently utilized. The anchored species may be immobilized by non-covalent or covalent attachments. Non-covalent attachment may be accomplished simply by coating the solid surface with a solution of the target gene product or binding partner, and optionally drying. Alternatively, an immobilized antibody specific for the species to be anchored may be used to anchor the species to the solid surface. The surfaces may be prepared in advance and stored according to procedures well known in the art.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the target gene protein and the interactive cellular or extracellular binding partner is prepared in which either the target gene product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt target gene protein/cellular or extracellular binding partner interaction can be identified.

In a particular embodiment, the target gene product can be prepared for immobilization using recombinant DNA techniques routinely used in the art. For example, the target gene coding region can be fused to a glutathione-S-transferase (GST) gene using a fusion vector, such as pGEX-5X-1, in such a manner that its binding activity is maintained in the resulting fusion protein. The interactive cellular or extracellular binding partner can be purified and used to raise a monoclonal antibody, using methods routinely practiced in the art and described above, in Section 5.2. This antibody can be labeled with the radioactive isotope $^{125}$I, for example, by methods routinely practiced in the art. In a heterogeneous assay, e.g., the GST-target gene fusion protein can be anchored to glutathione-agarose beads. The interactive cellular or extracellular binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the target gene protein and the interactive cellular or extracellular binding partner can be detected by measuring the amount of radioactivity that remains associated with the glutathione-agarose beads. A successful inhibition of the interaction by the test compound will result in a decrease in measured radioactivity.

Alternatively, the GST-target gene fusion protein and the interactive cellular or extracellular binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the target gene product/binding partner interaction can be detected by adding the labeled antibody and measuring the radioactivity associated with the beads. Such cyclophilin fusion protein constructs are similarly useful to identify and isolate cellular cyclophilin binding partners and mutants thereof, useful in the context of the present invention.

In another embodiment of the invention, these same techniques can be employed using peptide fragments that correspond to the binding domains of the target gene protein and/or the interactive cellular or extracellular binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the for the cellular or extracellular binding partner is obtained, short gene segments can be engineered to express peptide fragments of the protein, which can then be tested for binding activity and purified or synthesized.

For example, and not by way of limitation, a target gene product can be anchored to a solid material as described, above, in this Section by making a GST-target gene fusion protein and allowing it to bind to glutathione agarose beads. The interactive cellular or extracellular binding partner can be labeled with a radioactive isotope, such as $^{35}$S, and cleaved with a proteolytic enzyme such as trypsin. Cleavage products can then be added to the anchored GST-target gene fusion protein and allowed to bind. After washing away unbound peptides, labeled bound material, representing the cellular or extracellular binding partner binding domain, can be eluted, purified, and analyzed for amino acid sequence by well-known methods. Peptides so identified can be produced synthetically or fused to appropriate facilitative proteins using recombinant DNA technology.

5.7. PHARMACEUTICAL FORMULATIONS AND ROUTES OF ADMINISTRATION

The compounds of the present invention, including but not limited to, anti-cyclophilin antibodies, recombinant cyclophilin, derivatized cyclosporin and derivatized cyclophilin A, have utility in pharmacological compositions for the treatment and prevention of HIV-infection. Those compounds identified in the screening assays of the invention which inhibit the interaction between cyclophilin A and its cellular binding partner or receptor, also have utility in pharmacological compositions for the treatment and prevention of HIV-infection.

A compound of the invention can be administered to a human patient by itself or in pharmaceutical compositions where it is mixed with suitable carriers or excipients at doses to treat or ameliorate various conditions involving HIV-infection. A therapeutically effective dose further refers to that amount of the compound sufficient to inhibit HIV infection. Therapeutically effective doses may be administered alone or as adjunctive therapy in combination with other treatments for HIV infection or associated diseases. Techniques for the formulation and administration of the compounds of the instant application may be found in "Remington's Pharmaceutical Sciences" Mack Publishing Co., Easton, Pa., latest addition.

5.7.1. ROUTES OF ADMINISTRATION

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation.

Furthermore, one may administer the agent of the present invention in a targeted drug delivery system, for example in a liposome coated with an anti-CD4 antibody. The liposomes will be targeted to and taken up selectively by cells expressing CD4.

5.7.2. COMPOSITION/FORMULATION

The pharmaceutical compositions of the present invention may be manufactured in a manner that is itself known, e.g., by means of conventional mixing, dissolving, dragee-making, levitating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers, such as Hank's solution, Ringer's solution, or physiological saline buffer. For transmucosal administration, penetrants appropriate to the barrier to be permeated are used in the formulation. Such penetrants are usually known in the art.

For oral administration, the compounds can be formulated readily by combining the active compounds with pharmaceutically acceptable carriers well known to those in the art.

Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Liposomes and emulsions are well known examples of delivery vehicles or carriers for hydrophobic drugs. Certain organic solvents such as dimethylsulfoxide also may be employed, although usually at the cost of greater toxicity.

Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention identified as inhibitors of the interaction between cyclophilin A and its host receptor may be provided as salts with pharmaceutically compatible counterions. Pharmaceutically compatible salts may be formed with many acids, including but not limited to hydrochloric, sulfuric, acetic, lactic, tartaric, malic, succinic, etc.; or bases. Salts tend to be more soluble in aqueous or other protonic solvents that are the corresponding free base forms. Examples of pharmaceutically acceptable salts, carriers or excipients are well known to those skilled in the art and can be found, for example, in Remington's Pharmaceutical Sciences, 18th Edition, A. R. Gennaro, Ed., Mack Publishing Co., Easton, Pa., 1990. Such salts include, but are not limited to, sodium, potassium, lithium, calcium, magnesium, iron, zinc, hydrochloride, hydrobromide, hydroiodide, acetate, citrate, tartrate, malate sales, and the like.

5.7.3. EFFECTIVE DOSAGE

Pharmaceutical compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. Such information can be used to more accurately determine useful doses in humans.

A therapeutically effective dose refers to that amount of the compound that results in a reduction in the intensity of the infection or in amelioration of symptoms or a prolongation of survival in a patient. Toxicity and therapeutic efficacy of such compounds can be determined by standard pharmaceutical, pharmacological, and toxicological procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from cell culture assays or animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p. 1).

Dosage amount and interval may be adjusted individually to provide plasma levels of the active moiety which are sufficient to maintain the desired modulating effects, or minimal effective concentration (MEC). The MEC will vary for each compound but can be estimated from in vitro data; e.g., the concentration necessary to achieve a 50–90% inhibition of HIV infection using the assays described herein. Dosages necessary to achieve the MEC will depend on individual characteristics and route of administration. However, HPLC assays, bioassays or immunoassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

In immunization procedures, the amount of immunogen to be used and the immunization schedule will be determined by a physician skilled in the art and will be administered by reference to the immune response and antibody titers of the subject.

5.7.4. PACKAGING

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

6. EXAMPLE

ANTI-HIV ACTIVITY OF RECOMBINANT CYCLOPHILIN

The following in vitro experiments and assays demonstrate the effectiveness of recombinant cyclophilin to inhibit HIV infection of human peripheral blood lymphocytes (PBLs) or cultures of the H9 T cell line. Monitoring the progression of the infection will identify the effective dose range of soluble recombinant cyclophilin to interfere with infection.

6.1. MATERIALS AND METHODS

Cloning of murine cyclophilin. Mouse cyclophilin (cyclophilin A) was cloned from RAW 264.7 cells. Macrophages plated at a cell density of $1 \times 10^6$ cells/ml in RPMI/10% FBS were stimulated with LPS at 1 µg/ml. Six hours after the addition of LPS the medium was removed and total RNA isolated with RNAzol (Biotecx; Houston, Tex.) according to the manufacturer's instructions. One microgram of RNA was reverse transcribed, and resulting cDNA amplified by PCR using a set of cyclophilin-specific primers (5'-CCA-TGG-TCA-ACC-CCA-CC-3' (SEQ ID No:1) and 5'-ACG-CTC-TCC-TGA-GCT-ACA-GA-3' (SEQ ID No:2)) which span the cyclophilin coding region. A single DNA amplification product of the expected size was obtained, cloned into the plasmid pT7Blue and transformed into Nova Blue competent *E. coli* using the pT7Blue T-Vector Kit (Novagen; Madison, Wis.).

Expression and purification of recombinant murine cyclophilin. The recombinant pT7Blue clone containing murine cyclophilin cDNA was digested with the restriction enzymes NdeI and BamHI, and the cyclophilin insert was isolated and ligated in the NdeI/BamHI-digested pET14b vector (Novagen) allowing for its expression as a histidine fusion protein. The cyclophilin insert is placed behind the T7 promoter which is under the control of the lac repressor (allowing for induction by the addition of IPTG to the medium). The vector also contains the gene for ampicillin resistance (allowing for selection in carbenicillin-containing medium). The cyclophilin-containing vector was used to transform *E. coli* DH5α cells. These cells were streaked out, and cells grown up from a single recombinant colony were isolated and stored in 20% glycerol at −70° C. for later use. Murine cyclophilin-containing pET14b plasmid DNA was then prepared and used to transform *E. coli* BL21(DE3) expression strain (Novagen). One hundred milliliter cultures (seeded in 500 ml erlenmeyer flasks) were grown at 37° C. with vigorous shaking until the absorbance at 600 nm was between 0.6 and 1.0 OD units. At that time, IPTG was added to the cultures (1 mM final) and the incubation continued at 37° C. for an additional 3 hours. Bacteria were harvested by centrifugation and the cell pellets frozen at −70° C.

For protein purification, a bacterial pellet (corresponding to 100 mls of culture) was thawed and resuspended in 4.0 ml Binding Buffer in preparation for subsequent purification using His-Bind Resin which binds the histidine-rich sequence at the amino terminus of the fusion protein (Novagen). The bacteria were lysed by adding an equal volume of washed glass beads (106 $\mu$m; Sigma) and vortexing the mixture vigorously for 10 minutes. Glass beads were removed by centrifugation at 1000×g for 10 minutes, and the bacterial extract clarified by centrifugation at 38000×g for 30 min. The cleared bacterial lysate was sterile-filtered through a 0.22 micron syringe filter, and immediately loaded onto a column containing 2.5 ml His-Bind Resin (Novagen). The column was washed extensively according to the manufacturers directions.

After washing, the recombinant material was eluted with 1M imidazole. The eluate, which contained the cyclophilin fusion protein as assessed by SDS-PAGE, was subjected to proteolytic cleavage with thrombin to remove the His-Tag leader sequence from the amino terminus of the expressed peptide. For the cleavage reaction, thrombin (0.5 Units per mg recombinant protein) and the recombinantly expressed peptide were incubated in Thrombin Cleavage Buffer (20 mM Tris-HCl, pH 8.4, 150 mM NaCl and 2.5 mM $CaCl_2$) for 2 hours at 20° C. The mixture was then concentrated using a Centriprep-10 concentration device (Amicon Corp., Danvers, Mass.) at 4° C. To purify recombinant murine cyclophilin away from both thrombin and the cleaved His-Tag leader sequence, the concentrated mixture was subjected to high performance gel filtration chromatography over a Superose 12 column (Pharmacia, Piscataway, N.J.) equilibrated in PBS, pH 7.4. Cyclophilin eluted as a sharp peak with an apparent molecular mass of 19 kDa. Fractions containing cyclophilin (16 & 17) were pooled, concentrated using a Centriprep-10 concentration device (Amicon Corp.), and dialyzed against 0.01M sodium phosphate buffer, pH 7.4. Protein concentration was measured by Bradford assay with bovine gamma globulin as standard (Bio-Rad Laboratories, Richmond, Calif.). The material was greater than 98% pure as judged from silver-stained SDS polyacrylamide gels.

Cells and infection with HIV-1. H9 T cell line is cultured in RPMI medium supplemented with 10% fetal calf serum and 1% pen/strep. Cells are seeded at a density of $0.5×10^6$ cells/ml and, every 2nd day, one-half of the cell suspension is removed and replaced with fresh medium, to keep cell density below $1×10^6$ cells/ml. Cells are infected with HIV-$1_{RF}$ strain at a multiplicity index of 10 ng p24 per $1×10^6$ cells. After a 2 hr adsorption at 37° C., 5% $CO_2$, non-bound virus is washed out, and incubation is continued in fresh medium with or without rCyP at the indicated doses. Samples are removed for RT and p24 analysis (according to standard methods) every 2nd day, and half of the cell suspension substituted with fresh medium at that time.

Cultures of purified normal human peripheral blood lymphocytes (PBLs) are activated/stimulated with PHA/IL-2 for 48 hours prior to infection. Cultures are then infected with HIV in the presence or absence of exogenous recombinant cyclophilin (rCyP) and re-fed every three days with rCyP containing medium at the indicated doses. Monitoring the progression of the infection will identify the effective dose range of soluble cyclophilin to interfere with HIV infection (presumably by competitive inhibition of a requisite binding interaction between CyP and its cellular "receptor").

Figure 2:
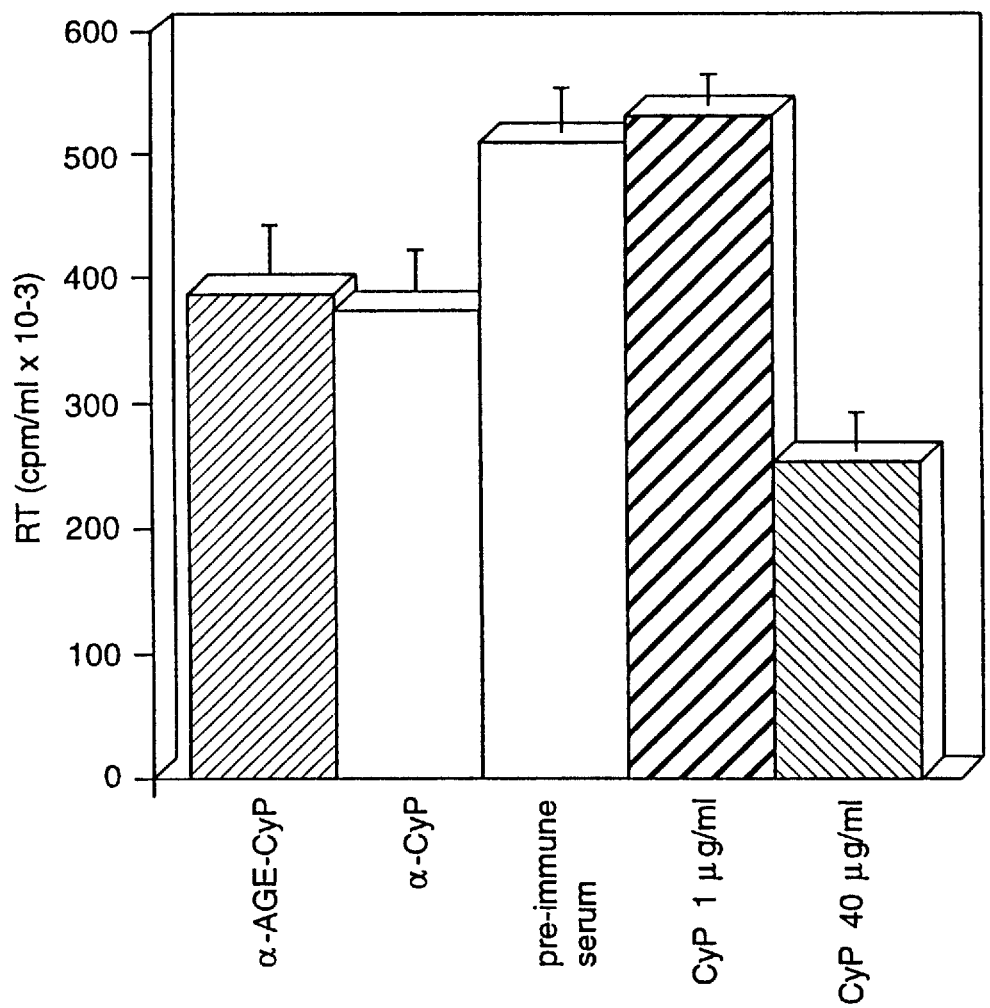
Figure 3:
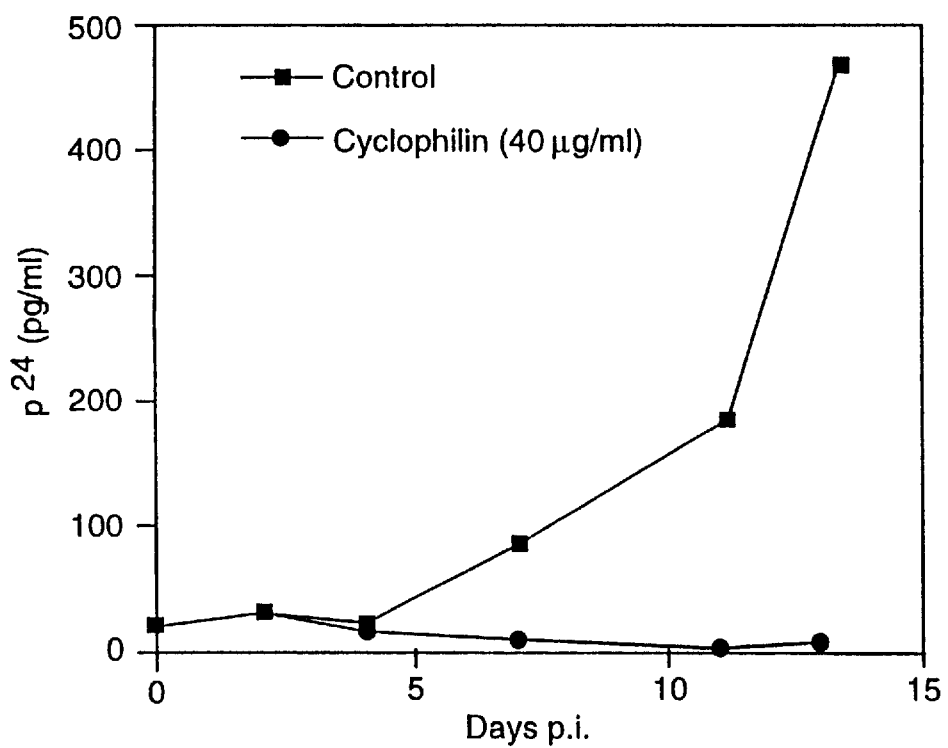

The results of these studies are illustrated in FIGS. 1, 2 and 3. FIG. 1 illustrates that on day 5 after infection, as assayed by RT activity in the culture supernatants, experimental HIV infection is inhibited in H9 T cell cultures treated with recombinant murine cyclophilin at 40 $\mu$g/ml. FIG. 2 shows in part that the presence of cyclophilin at 40 $\mu$g/ml, but not at 1 $\mu$g/ml, inhibits HIV infection in H9 cell cultures, as measured by RT activity post-infection. In additional experiments, these inhibitory effects seen with a cultured T cell line were confirmed and extended to normal human peripheral blood lymphocyte cultures, reinforcing the utility of this therapeutic modality against HIV infection in humans. FIG. 3 shows a time course of the inhibitory effect of exogenously supplied recombinant cyclophilin at a dose of 40 $\mu$g/ml in PBL cultures, as measured by the appearance of p24 antigen in culture supernatants as assayed by a commercially available p24 ELISA kit.

7. EXAMPLE

ANTI-HIV ACTIVITY OF ANTI-CYCLOPHILIN ANTIBODIES

The following in vitro experiments and assays demonstrate the effectiveness of antibodies raised against cyclophilin (anti-CyP) or against an experimentally glycated preparation of CyP (anti-AGE-CyP). The anti-AGE-CyP antibodies recognize soluble CyP in its native configuration as indicated by immunoprecipitation studies; the anti-CyP antiserum did not.

7.1. MATERIALS AND METHODS

AGE-modification of murine cyclophilin. An aliquot of purified recombinant murine cyclophilin (500 $\mu$g/ml final) was reacted with glucose (1M final) in 0.5M sodium phosphate buffer (pH 7.4) for three months at 37° C. in a non-humidified air incubator. Incubation of proteins with glucose under these conditions has been shown to lead to the formation of irreversible covalent adducts, known as Advanced Glycation Endproducts (or AGEs), via the extended system of Maillard reactions that lead to the spontaneous modification of proteins by reducing sugars.

Upon completion, the reaction mixture was dialyzed to remove non-covalently attached low molecular weight reactants, aliquoted into eppendorf tubes (0.125 μg per tube), and stored frozen at −20° C. until used for immunization of rabbits.

Generation of rabbit anti-cyclophilin antisera: Polyclonal rabbit anti-cyclophilin antisera were raised as follows. Female New Zealand White rabbits were immunized with cyclophilin (origin and quantity of each preparation of cyclophilin used is described in detail below) which has been emulsified in 1.0 ml saline plus 1.0 ml complete Freund's adjuvant. The immunogen was administered by subcutaneous injection at four sites on the dorsum of the rabbit. Animals were administered booster injections monthly with the same antigen emulsified in 1.0 ml saline and 1.0 ml incomplete Freund's adjuvant. Blood was withdrawn 7 days and 14 days following each booster injection, and the serum fraction was recovered and stored frozen at −20° C.

anti-human cyclophilin antisera. The recombinant human cyclophilin used for immunization and boosting of rabbits was obtained from Dr. Handschumacher (Yale University; New Haven, CT). At each time point, rabbits were immunized or boosted with 20 μg human cyclophilin. Pre-immune and immune sera were tested for reactivity by Western blotting and immunoprecipitation against both recombinant human cyclophilin and recombinant murine cyclophilin. Pre-immune sera were negative in both assays. On western blots the immune sera was positive against both antigens. Immunoprecipitation experiments were negative.

anti-murine cyclophilin antisera. The recombinant murine cyclophilin used for immunization and boosting was produced in E. coli by the procedure described above. At each time point, rabbits were immunized and boosted with 50 μg murine cyclophilin. Pre-immune and immune sera were tested for reactivity by Western blotting and immunoprecipitation against both recombinant human cyclophilin and recombinant murine cyclophilin. Pre-immune sera were negative in both assays. On western blots the immune sera was positive against both antigens. Immunoprecipitation experiments were negative.

anti-AGE-modified murine cyclophilin antisera. At each time point, rabbits were immunized and boosted with 125 μg AGE-modified murine cyclophilin. Pre-immune and immune sera were tested for reactivity by Western blotting and immunoprecipitation against both recombinant human cyclophilin and recombinant murine cyclophilin. Pre-immune sera were negative in both assays. On western blots and in immunoprecipitation experiments the immune sera was positive against both antigens indicating that antibody raised against AGE-modified murine cyclophilin recognized soluble cyclophilin (presumably in its native conformation), as well as, immobilized (and presumably denatured) cyclophilin.

Preparation on murine cyclophilin affinity resin. To prepare a cyclophilin affinity resin, recombinant murine cyclophilin was coupled to Sepharose beads according to a protocol recommended by the manufacturer. In brief, three grams of freeze-dried CNBr-activated Sepharose 4B (Pharmacia; Piscataway, N.J.) was rehydrated in 1 mM HCl (yielding 10.5 ml swollen gel), and washed for 15 minutes with 1 mM HCl (200 ml/g freeze dried powder) on a sintered glass funnel. Following the removal of fluid on the sintered glass funnel, 5.0 ml gel was transferred to a 50 cc tube and was mixed with 10 ml of 0.1M $NaHCO_3$/0.5M NaCl (pH 8.0) containing 25 mg of recombinant murine cyclophilin. The mixture was rocked at room temperature for 2 hours. At that time, 0.5 ml of 1M ethanolamine-HCl (pH 9) was added to quench excess reactive groups, and rocking was continued for another 2 hours. The binding of cyclophilin to the gel matrix was essentially complete, as indicated by the absence of detectable protein in the supernatant. The gel was then transferred to a sintered glass funnel and washed with three alternate cycles of 0.1M sodium acetate (pH 4.0) containing 0.5M NaCl and 0.1M Tris-HCl (pH 8.0) containing 0.5M NaCl (40 ml each wash). The final volume of swollen gel was about 5.0 ml.

Affinity purification of rabbit anti-AGE-modified murine cyclophilin. Murine cyclophilin affinity resin (5.0 ml packed volume) which was prepared according to the procedure described above was transferred to a 10 ml glass walled chromatography column. After allowing the resin to pack, the column was washed successively with 10 bed-volumes of 10 mM Tris (pH 7.5), 10 bed-volumes of 100 mM glycine (pH 2.5), 10 bed-volumes 10 mM Tris (pH 8.8), 10 bed-volumes 100 mM triethylamine (pH 11.5, prepared fresh), and lastly, 10 bed-volumes 10 mM Tris (pH 7.5). Five milliliters polyclonal rabbit anti-murine AGE-modified cyclophilin which had been dialyzed overnight against 10 mM Tris (pH 7.5) was loaded onto the column. The column was washed with 10 bed-volumes 20 mM Tris (pH 7.5), followed by 10 bed-volumes 10 mM Tris/0.5M NaCl (pH 7.5), and then cyclophilin specific antibodies were eluted by washing the column with 100 mM glycine-HCl (pH 2.5) and collecting 1.0 ml fractions.

Cells and infection with HIV-1. H9 T cell line was cultured in RPMI medium supplemented with 10% fetal calf serum and 1% pen/strep. Cells were seeded at a density of $0.5 \times 10^6$ cells/ml and, every 2nd day, one-half of the cell suspension was removed and replaced with fresh medium, to keep cell density below $1 \times 10^6$ cells/ml. Cells were infected with HIV-$1_{RF}$ strain at a multiplicity index of 10 ng p24 per $1 \times 10^6$ cells. After a 2 hr adsorption at 37° C., 5% $CO_2$, non-bound virus was washed out, and incubation was continued in fresh medium. Samples were removed for RT and p24 analysis every 2nd day, and half of the cell suspension substituted with fresh medium at that time.

Monocyte cultures were prepared from the whole blood of HIV-negative donors. Peripheral blood mononuclear cells (PBMCs) were isolated on a Ficoll-Hypaque gradient, resuspended at $6-8 \times 10^6$ cells/ml in DMEM supplemented with 10% heat-inactivated normal human serum (NHS) and plated in a PRIMARIA flask. After a 2 h, 37° incubation, adherent cells were washed 3 times with DMEM, and re-fed with DMEM+10% NHS +1 ng/ml M-CSF (Sigma). After a 24 h incubation, cells were washed with $Ca^{++}$- and $Mg^{++}$-free PBS and then incubated in PBS+10 mM EDTA for 3–5 min on ice. Cells were detached with a rubber policeman, washed, counted, and resuspended in DMEM+10% NHS+1 ng/ml M-CSF. At that point, cells were >98% monocytes by the criteria of cell morphology and nonspecific esterase staining. Monocytes were plated at a density $10^6$ cells/ml in PRIMARIA plates and allowed to differentiate in vitro for 6 days with half the medium changed every 2 days. On day 7 after plating, cells were exposed to a monocytotropic strain HIV-$1_{ADA}$ (multiplicity of infection 100 ng of p24 per $10^6$ cells) for 2 hr, washed, and cultured in DMEM+10% NHS.

Treatment with cyclophilin and α-cyclophilin antibodies. Recombinant mouse cyclophilin at various concentrations (ranging from 1 to 200 μg/ml), and anti-cyclophilin antibodies (1:40 dilution) were added to cells together with the virus, and were likewise present throughout all subsequent incubations.

Quantitative PCR analysis. At various intervals after infection, cells were washed and resuspended in 1×PCR buffer with Proteinase K (50 mM KCl; 10 mM Tris-HCl, pH 8.3; 2.5 mM $MgCl_2$; 0.1 mg/ml gelatin; 0.45% NP40; 0.45% Tween 20; 250 µg/ml Proteinase K) at $6\times10^6$ cells/ml. After a 3 hr digestion at 60° C., Proteinase K was inactivated by heating to 95° C. for 10 min., and lysates were used for PCR analysis with primers specific for the HIV-1 pol gene (PCR I and PCR J), HIV pol PCR primers: sense, 5'-GAAGCTCTATTAGATACAGG-3' (SEQ ID No:3); antisense, 5'-TCCTGGCTTTAATTTTACTGG-3' (SEQ ID No:4); probe, 5'-GGAATTGGAGGTTTATCAAAGT-3' (SEQ ID No:5); HIV-1 2-LTR circle DNA, or cellular α-tubulin gene as a control (AT1 and AT2). PCR reactions in 50 µl were prepared as follows: 25 µl cell lysate; 1 µl of 10 mM dNTP mixture; 1 µl of each primer; 12.5 µl of 2×PCR buffer without Proteinase K; 0.25 µl of Taq polymerase (5 U/µl or 1.25 U per reaction). 35 cycles of PCR were performed, each composed of 30 sec, 95° C. denaturation; 30 sec, 60° C. annealing; 45 sec, 72° C. extension. Cycles were preceded by a 6 min, 95° C. denaturation, and followed by a 7 min, 72° C. final extension. PCR products were visualized by hybridization to a $^{32}$P-labeled probe after a Southern transfer, and results were quantitated on a direct imager system (Packard).

7.2. RESULTS

In H9 cell cultures (FIG. 2), antisense raised against recombinant cyclophilin or glycated cyclophilin inhibited HIV infection as measured by RT activity 3 days post-infection. To confirm and extend these results using non-transformed cells, additional experiments were performed in cultures of normal human monocytes/macrophages.

In cultures of non-adherent PBMCs, reverse transcriptase activity in the supernatants was assayed at days 3 and 5 after infection. Both anti-AGE and anti-cyclophilin affinity purified antibodies decreased RT activity in the supernatants of HIV-infected H9 cell cultures at day 3 after infection (FIG. 1). Cyclophilin at 1 µg/ml did not show any effect on HIV-1 replication; however, when concentration of cyclophilin was increased to 40 µg/ml, there was a marked anti-viral activity (FIG. 1). This antiviral effect was even more pronounced at day 5 after infection (FIG. 2).

Figure 4:
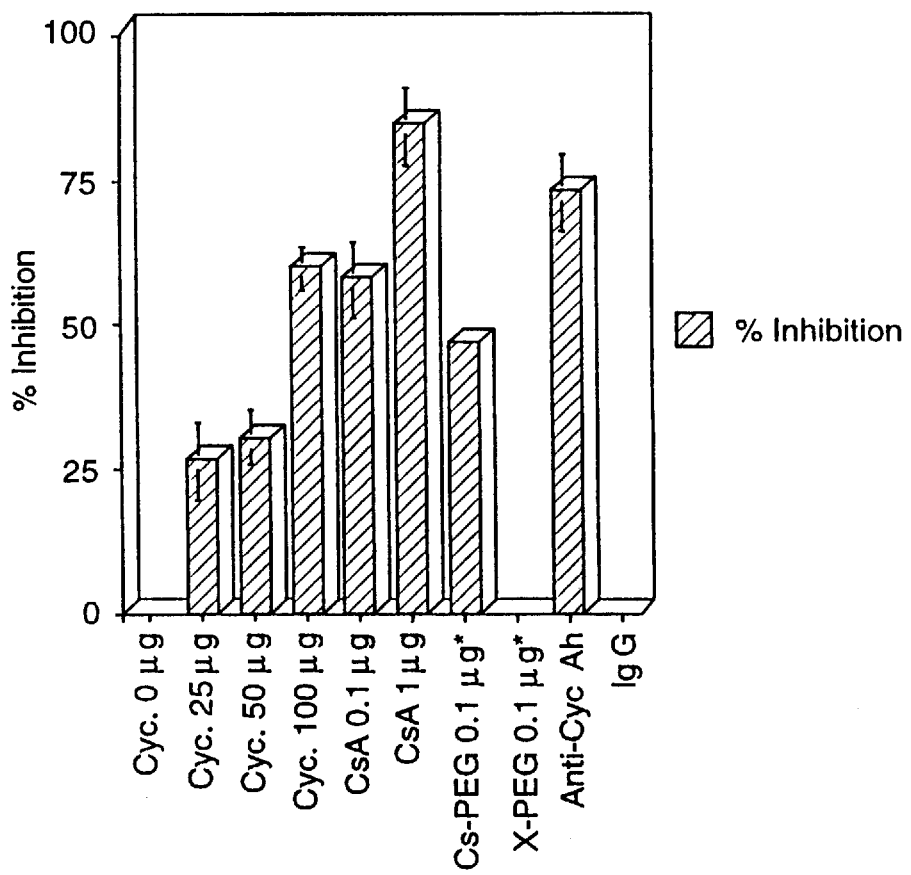

The effects in monocyte cultures were assayed by PCR 48 hr after infection. A dose-dependent inhibition of HIV-1 cDNA synthesis by cyclophilin was observed (FIG. 3), with 50% inhibition ($IC_{50}$) at 50 µg/ml. Importantly, inhibition was mostly seen for HIV-1 cDNA forms produced late in reverse transcription process (after the second strong stop), with almost no effect on the first strong stop cDNA (FIG. 3). This result suggests that uncoating of HIV-1, rather than virus entry, was affected in this experiment. Similar results were observed with anti-cyclophilin antibodies (FIG. 4).

8. EXAMPLE

ANTI-HIV ACTIVITY OF A PEGYLATED CYCLOSPORIN ANALOG

The following in vitro experiments and assays demonstrate the effectiveness of pegylated cyclosporin as an inhibitor of HIV-infection. Human monocyte/macrophage cell cultures are challenged with an inoculum of HIV in the presence and absence of a "pegylated" cyclosporin analogue. This cyclosporin analogue has been modified by a reaction with polyethylene glycol so as to prevent cell entry. This pegylated CsA is not immunosuppressive in a standard T cell proliferation assay. Monitoring the progression of the infection will identify the effective dose range of pegylated cyclosporin to interfere with HIV infection.

8.1. MATERIALS AND METHODS

Preparation of Pegylated Cyclosporin. Replication of HIV virions, which have been shown to contain cyclophilin, are inhibited by the immunosuppressive drug, cyclosporin A (CsA). To determine whether CsA acts extracellularly or intracellularly in this regard, a CsA analogue which cannot penetrate the cell membrane has been synthesized as follows: 8-amino-cyclosporin A (0.5 mgs) was reacted with methoxypolyethylene glycol-succinimidyl succinate (10 mgs) and 4-dimethylamino pyridine (0.2 mgs) in methylene chloride with stirring for two days at room temperature in the dark. To block any unreacted sites, ethanolamine (5 µl) was then added and the mixture incubated at room temperature with stirring for another 24 hours. The reaction mixture was transferred to −70° C. until CsA-PEG purification by normal phase HPLC was performed.

Cells and infection with HIV-1. H9 T cell line is cultured in RPMI medium supplemented with 10% fetal calf serum and 1% pen/strep. Cells are seeded at a density of $0.5\times10^6$ cells/ml and, every 2nd day, one-half of the cell suspension is removed and replaced with fresh medium, to keep cell density below $1\times10^6$ cells/ml. Cells are infected with HIV-$1_{RF}$ strain at a multiplicity index of 10 ng p24 per $1\times10^6$ cells. After a 2 hr adsorption at 37° C., 5% $CO_2$, non-bound virus is washed out, and incubation is continued in fresh medium. Samples are removed for RT and p24 analysis every 2nd day, and half of the cell suspension substituted with fresh medium at that time.

Monocyte cultures are prepared from the whole blood of HIV-negative donors. Peripheral blood mononuclear cells (PBMCS) are isolated on a Ficoll-Hypaque gradient, resuspended at $6-8\times10^6$ cells/ml in DMEM supplemented with 10% heat-inactivated normal human serum (NHS) and plated in a PRIMARIA flask. After a 2 h, 37° incubation, adherent cells are washed 3 times with DMEM, and re-fed with DMEM+10% NHS+1 ng/ml M-CSF (Sigma). After a 24 h incubation, cells are washed with $Ca^{++}$- and $Mg^{++}$-free PBS and then incubated in PBS+10 mM EDTA for 3–5 min on ice. Cells are detached with a rubber policeman, washed, counted, and resuspended in DMEM+10% NHS+1 ng/ml M-CSF. At that point, cells are >98% monocytes by the criteria of cell morphology and nonspecific esterase staining. Monocytes are plated at a density $10^6$ cells/ml in PRIMARIA plates and allowed to differentiate in vitro for 6 days with half the medium changed every 2 days. On day 7 after plating, cells are exposed to a monocytotropic strain HIV-$1_{ADA}$ (multiplicity of infection 100 ng of p24 per $10^6$ cells) for 2 hr, washed, and cultured in DMEM+10% NHS.

As shown in FIG. 4, cyclosporin derivatized to inhibit cell entry was effective at a dose of 0.1 µg/ml to inhibit HIV infection of monocyte/macrophage cultures as judged by PCR analysis of HIV pol gene retrotranscription. Although pegylated CsA was non-immunosuppressive, it showed approximately the same antiviral effect as CsA itself, a potent immunosuppressor, suggesting that the anti-viral effects of pegylated CsA arise through different molecular interactions than support immunosuppression.

In a parallel study with H9 cells, pegylated CsA was also approximately equipotent with CsA (data not shown), suggesting the therapeutic effects of derivatized CsA in various HIV-susceptible cell types.

9. EXAMPLE

CROSS-LINKING OF $^{125}$I-LABELED MURINE CYCLOPHILIN TO MEMBRANE PROTEINS ON H9 CELLS.

Cross-linking studies represent a first step toward determining the identity of cyclophilin-binding partners on H9 cell membranes. Disuccinimidyl suberate (DSS), a homo-bifunctional N-hydroxy-succinimide ester, is used as a cross-linking reagent. H9 cells are harvested, washed in ice-cold PBS, $2.5 \times 10^7$ cells transferred to a clean tube, and cells pelleted by centrifugation. This pellet is resuspended in 0.5 ml cross-linking buffer, and $^{125}$I-cyclophilin added. After a 60 minute incubation on ice, cells are pelleted at 500×g, and supernatant discarded. The pellet is resuspended to $2.5 \times 10^6$ cells/ml in crosslinking buffer, and DSS added to a final concentration of 20 ug/ml. This reaction mixture is rocked at 4° C. for 20 minutes, at which time 1 volume of TE buffer, pH 7.4 is added to stop the reaction. Cells are washed 3 times in ice-cold TE buffer (pH 7.4), and membranes extracted by homogenization in an NP40 lysis buffer. NP40 extracts are analyzed by SDS-PAGE electrophoresis and autoradiography to identify proteins crosslinked to iodinated cyclophilin. Additional analyses, in which cells are fractionated into membrane, cytosolic, and/or nuclear fractions by standard methods are employed to further characterize the subcellular localization of cyclophilin-binding partners.

Iodination of recombinant murine cyclophilin. Recombinant murine cyclophilin may be iodinated using the Bolton-Hunter method (Parker, 1990), or the commercially available Iodogen method. Bolton-Hunter reagent (N-succinimidyl-3-(4-hydroxy-5-([$^{125}$I]iodophenyl-propionate) will be purchased from NEN.

10. EXAMPLE GENERATION OF MONOCLONAL ANTIBODIES TO AGE-MODIFIED MURINE CYCLOPHILIN.

An immunization protocol to generate monoclonal anti-AGE-modified cyclophilin begins with immunization of mice. Four BALB/C mice were immunized by i.p. injection with 25 µg AGE-modified murine cyclophilin in 1:1 mixture of saline and Ribi adjuvant (prepared according to the recommendations of the manufacturer). Twenty-one days post-immunization, mice were boosted with 25 µg AGE-modified murine cyclophilin in RIBI adjuvant, and mice are boosted with this amount of antigen in RIBI adjuvant every 21 days. After the second boost, mice are tail-bled (approximately 50 µl) and the serum from each mouse analyzed for immunoreactivity against cyclophilin in a direct ELISA in which the plate is coated with recombinant murine cyclophilin. When a mouse screens positive for anticyclophilin IgG, the mouse will given a final boost of antigen and then be euthanized for spleen removal and hybridoma production according to methods well-known in the art. Resulting hybridomas are screened for production of cyclophilin-specific monoclonal antibodies.

The present invention is not to be limited in scope by the specific embodiments described which are intended as single illustrations of individual aspects of the invention, and functionally equivalent methods and components are within the scope of the invention. Indeed various modifications of the invention, in addition to those shown as described herein will become apparent to those skilled in the art from the foregoing description and accompanying drawings. Such modifications are intended to fall within the scope of the appended claims.

A number of references have been cited and the entire disclosures of which are incorporated herein by reference.

What is claimed is:

1. A method for reducing HIV titer comprising administering an effective amount of an anti-cyclophilin antibody to a subject.

2. The method of claim 1 in which the antibody is polyclonal.

3. The method of claim 1 in which the antibody is monoclonal.

4. The method of claim 1 in which the antibody is a single-chain antibody, chimeric antibody, humanized antibody, or Fab fragment.

* * * * *